(12) United States Patent
Al-Ali et al.

(10) Patent No.: US 9,863,009 B2
(45) Date of Patent: Jan. 9, 2018

(54) SEQUENCE SPECIFIC PRIMER POOL FOR MULTIPLEX PCR AND METHOD OF DETECTING MICROBIAL INFECTIONS IN THALASSEMIA PATIENTS

(71) Applicant: University of Dammam, Dammam (SA)

(72) Inventors: Amein Kadhem Al-Ali, Dhahran (SA); Francis Borgio Jesu Alexander, Khobar (SA); Zaki Naserullah, Qatif (SA); Sayed Abdul Azeez, Rakkah (SA); Sana Al-Jarrash, Qatif (SA)

(73) Assignee: University of Dammam, Dammam (SA)

( * ) Notice: Subject to any disclaimer, the term of this patent is extended or adjusted under 35 U.S.C. 154(b) by 527 days.

(21) Appl. No.: 14/518,413

(22) Filed: Oct. 20, 2014

(65) Prior Publication Data
US 2016/0083806 A1    Mar. 24, 2016

Related U.S. Application Data

(60) Provisional application No. 62/053,014, filed on Sep. 19, 2014.

(51) Int. Cl.
*C12Q 1/68* (2006.01)
(52) U.S. Cl.
CPC ........... *C12Q 1/6895* (2013.01); *C12Q 1/689* (2013.01); *C12Q 2600/16* (2013.01)
(58) Field of Classification Search
None
See application file for complete search history.

(56) References Cited

U.S. PATENT DOCUMENTS 6,610,836 B1 *   8/2003   Breton ................. C07K 14/26
                                                                 435/320.1
2008/0261222 A1  10/2008  Rogan

FOREIGN PATENT DOCUMENTS

| EP | 2363497 A2 | 9/2011 |
| JP | 04176146 B2 | 11/2008 |
| KR | 2010012319 A | 2/2010 |

OTHER PUBLICATIONS

Chang SS, Hsieh WH, Liu TS, Lee SH, Wang CH, Chou HC, Yeo YH, Tseng CP, Lee CC. Multiplex PCR system for rapid detection of pathogens in patients with presumed sepsis—a systemic review and meta-analysis. PLoS One. May 29, 2013; 8(5):e62323, pp. 1-10.*

El-Sherbeini M, Geissler WM, Pittman J, Yuan X, Wong KK, Pompliano DL. Cloning and expression of Staphylococcus aureus and Treptococcus pyogenes murD genes encoding uridine diphosphate N-acetylmuramoyl-L-alanine:D-glutamate ligases. Gene. Mar. 27, 1998; 210(1):117-25.*
Genbank Accession No. AF009671—Staphylococcus aureus UDP-N-acetylmuramoyl-L-alanine: D-glutamate ligase (murD) gene, complete cds (submitted by El-Sherbeini et al. Jun 20, 1997, retrieved on Feb. 27, 2017 from https://www.ncbi.nlm.nih.gov/nuccore/AF009671).*
Genbank Accession No. AJ251858—Candida albicans yst1 gene for YST1 protein, exons 1-2 (submitted Dec. 15, 1999, retrieved on Feb. 27, 2017 from https://www.ncbi.nlm.nih.gov/nuccore/AJ251858).*
Genbank Accession No. JN940584—Candida albicans strain Ph288 18S ribosomal RNA (SSU) gene, partial sequence (submitted Oct. 25, 2011, retrieved on Feb. 27, 2017 from https://www.ncbi.nlm.nih.gov/nuccore/JN940584).*
Laffler TG, Cummins LL, McClain CM, Quinn CD, Toro MA, Carolan HE, Toleno DM, Rounds MA, Eshoo MW, Stratton CW, Sampath R, Blyn LB, Ecker DJ, Tang YW. Enhanced diagnostic yields of bacteremia and candidemia in blood specimens by PCR-electrospray ionization mass spectrometry. J Clin Microbiol. Nov. 2013; 51(11):3535-41.*
Laffler et al. Supplementary material—Table S1. J Clin Microbiol. Nov. 2013; 51(11):3535-41.*
Lehmann LE, Hunfeld KP, Emrich T, Haberhausen G, Wissing H, Hoeft A, Stüber F. A multiplex real-time PCR assay for rapid detection and differentiation of 25 bacterial and fungal pathogens from whole blood samples. Med Microbiol Immunol. Sep. 2008; 197(3):313-24.*
Leitner E, Kessler HH, Spindelboeck W, Hoenigl M, Putz-Bankuti C, Stadlbauer-Köllner V, Krause R, Grisold AJ, Feierl G, Stauber RE. Comparison of two molecular assays with conventional blood culture for diagnosis of sepsis. J Microbiol Methods. Mar. 2013; 92(3):253-5.*
Lowe T, Sharefkin J, Yang SQ, Dieffenbach CW. A computer program for selection of oligonucleotide primers for polymerase chain reactions. Nucleic Acids Res. Apr. 11, 1990; 18(7):1757-61.*
Obara H, Aikawa N, Hasegawa N, Hori S, Ikeda Y, Kobayashi Y, Murata M, Okamoto S, Takeda J, Tanabe M, Sakakura Y, Ginba H, Kitajima M, Kitagawa Y. The role of a real-time PCR technology for rapid detection and identification of bacterial and fungal pathogens in whole-blood samples. J Infect Chemother. Jun. 2011; 17(3):327-33.*

* cited by examiner

*Primary Examiner* — Samuel Woolwine
*Assistant Examiner* — Olayinka Oyeyemi
(74) *Attorney, Agent, or Firm* — Oblon, McClelland, Maier & Neustadt, L.L.P.

(57) ABSTRACT

Reagents and methods for the fast, accurate and early detection of infections in thalassemia major patients. Reagents include a primer pool containing a mixture of primer pairs for the specific recognition and simultaneous amplification of targeted gene sequences of pathogens from a biological sample collected from a patient in a multiplex PCR reaction. Pathogens may include at least one Fungi species, *Klebsiella pneumoniae, Candida albicans* and *Staphylococcus aureus*. Subsequent identification of the pathogens is achieved by DNA sequencing analysis.

9 Claims, 3 Drawing Sheets

| | | | |
|---|---|---|---|
| Query | 1 | CGGCTACCACATCCAAGGAAGGCAGCAGGCGCGCAAATTACCCAATCCCGACACGGGGAG | 60 |
| Sbjct | 327 | CGGCTACCACATCCAAGGAAGGCAGCAGGCGCGCAAATTACCCAATCCCGACACGGGGAG | 386 |
| Query | 61 | GTAGTGACAATAAATAACGATACAGGGCCCTTTTGGGTCTTGTAATTGGAATGAGTACAA | 120 |
| Sbjct | 387 | GTAGTGACAATAAATAACGATACAGGGCCCTTTTGGGTCTTGTAATTGGAATGAGTACAA | 446 |
| Query | 121 | TGTAAATACCTTAACGAGGAACAATTGGAGGGCAAGTCTGGTGCCAGCAGCCGCGGTAAT | 180 |
| Sbjct | 447 | TGTAAATACCTTAACGAGGAACAATTGGAGGGCAAGTCTGGTGCCAGCAGCCGCGGTAAT | 506 |
| Query | 181 | TCCAGCTCCAAAAGCGTATATTAAAGTTGTTGCAGTTAAAAAGCTCGTAGTTGAACCTTG | 240 |
| Sbjct | 507 | TCCAGCTCCAAAAGCGTATATTAAAGTTGTTGCAGTTAAAAAGCTCGTAGTTGAACCTTG | 566 |
| Query | 241 | GGCTTGGCTGGCCGGTCCATCTTTTTGATGCGTACTGGACCCAGCCGAGCCTTTCCTTCT | 300 |
| Sbjct | 567 | GGCTTGGCTGGCCGGTCCATCTTTTTGATGCGTACTGGACCCAGCCGAGCCTTTCCTTCT | 626 |
| Query | 301 | GGGTAGCCATTTATGGCGAACCAGGACTTTTACTTTGAAAAAATTAGAGTGTTCAAAGCA | 360 |
| Sbjct | 627 | GGGTAGCCATTTATGGCGAACCAGGACTTTTACTTTGAAAAAATTAGAGTGTTCAAAGCA | 686 |
| Query | 361 | GGCCTTTGCTCGAATATATTAGCATGGAATAATAGAATAGGACGTTATGGTTCTATTTTG | 420 |
| Sbjct | 687 | GGCCTTTGCTCGAATATATTAGCATGGAATAATAGAATAGGACGTTATGGTTCTATTTTG | 746 |
| Query | 421 | TTGGTTTCTAGGACCATCGTAATGATTAATAGGGACGGTCGGGGTATCAGTATTCAGTT | 480 |
| Sbjct | 747 | TTGGTTTCTAGGACCATCGTAATGATTAATAGGGACGGTCGGGGTATCAGTATTCAGTT | 806 |
| Query | 481 | GTCAGAGGTGAAATTCTTGGATTTACTGAAGACTAACTACTGCGAAAGCATTTACCAAGG | 540 |
| Sbjct | 807 | GTCAGAGGTGAAATTCTTGGATTTACTGAAGACTAACTACTGCGAAAGCATTTACCAAGG | 866 |

FIG. 2

| | | | |
|---|---|---|---|
| Query | 1 | CAATAAGATAAGGCTTATGGAGCCAGTCATCTGCAGTCAGCGGCTCGGTCGGCGGGCTGT | 60 |
| Sbjct | 181163 | CAATAAGATAAGGCTTATGGCGCCAGTCATCTGCAGTCAGCGGCTCGGTCGGCGGGCTGT | 181104 |
| Query | 61 | TCCACGCATGCAGATGCATGCCGACTTCCGCGGTGCCGCGGGCAATCACGTCTCTGGCGA | 120 |
| Sbjct | 181103 | TCCACGCATGCAGATGCATGCCGACTTCCGCGGTGCCGCGGGCAATCACGTCTCTGGCGA | 181044 |
| Query | 121 | ATTCGATATAAAAGGGATCGATGGCCATTTCATAGTTGGTCAAATAGACCGGTTTAAAGC | 180 |
| Sbjct | 181043 | ATTCGATATAAAAGGGGTCGATGGCCATTTCATAGTTGGTCAAATAGACCGGTTTAAAGC | 180984 |
| Query | 181 | CATACTTTTCGCAAAGCTGCTGAAAACGCGGAAGATAACGCGCATTCTCGGTGGTGATGC | 240 |
| Sbjct | 180983 | CATACTTTTCGCAAAGCTGCTGAAAACGCGGAAGATAACGCGCATTCTCGGTGGTGATGC | 180924 |
| Query | 241 | TGTC | 244 |
| Sbjct | 180923 | TGTC | 180920 |

FIG. 3

```
Query      1        CTACTTTAGATGCAACATAACCAATATTGCCGGATAATCTTCCAGTTAAGCGACtttttt    60
                    ||||||||||||||||||||||||||||||||||||||||||||||||||||||||||||
Sbjct      1250159  CTACTTTAGATGCAACATAACCAATATTGCCGGATAATCTTCCAGTTAAGCGACTTTTTT    1250100

Query      61       tAAACATATCTCCAATTAGAGAAGTAACTGTCGTTTTACCATTTGTACCCGTTACAGCTA    120
                    ||||||||||||||||||||||||||||||||||||||||||||||||||||||||||||
Sbjct      1250099  TAAACATATCTCCAATTAGAGAAGTAACTGTCGTTTTACCATTTGTACCCGTTACAGCTA    1250040

Query      121      TGATTGGKGCTTCARARATWARATAACTTAACTCAACTTCTGTTAAAATTTTCAAACCTC    180
                    |||||||  ||||| |   |  | ||||||||||||||||||||||||||||||||||||
Sbjct      1250039  TGATTGGTGCTTCAGAGATTAGATAACTTAACTCAACTTCTGTTAAAATTTTCAAACCTC    1249980

Query      181      GTTTCMCTGCTTCATCAATAATAGATACTGTATAAGGTATTCCAGGATTTTTAACAATTA    240
                    |||| |||||||||||||||||||||||||||||||||||||||||||||||||||||||
Sbjct      1249979  GTTTCACTGCTTCATCAATAATAGATACTGTATAAGGTATTCCAGGATTTTTAACAATTA    1249920

Query      241      TTGGATTATTATCAAGCAACGTTAATGGATGACTTCCACTTACAACARAAATGCCCATAR    300
                    ||||||||||||||||||||||||||||||||||||||||||||||||| |||||||||
Sbjct      1249919  TTGGATTATTATCAAGCAACGTTAATGGATGACTTCCACTTACAACAGAAATGCCCATAG    1249860

Query      301      ATTCTAAATCTTTTGCATGAGCATCTTGKGATAAGTCTTTTCCATCATTGACAGTTACAT    360
                    |||||||||||||||||||||||||||| |||||||||||||||||||||||||||||||
Sbjct      1249859  ATTCTAAATCTTTTGCATGAGCATCTTGTGATAAGTCTTTTCCATCATTGACAGTTACAT    1249800

Query      361      TCGCACCTAATTTACTTAATAATTTAGCTGCTTCATAACCACTTTTTGCCAAAC    414
                    |||||||||||||||||||||||||||||||||||||||||||||||||||||
Sbjct      1249799  TCGCACCTAATTTACTTAATAATTTAGCTGCTTCATAACCACTTTTTGCCAAAC    1249746
```

FIG. 4

```
Query      1        TTTGTATTGATGTTGAGATCTTACTATCTTTAACTATGCGCACACAATAAAtttttttt    60
                    ||||||||||||||||||||||||||||||||||||||||||||||||||||||||||||
Sbjct      579      TTTGTATTGATGTTGAGATCTTACTATCTTTAACTATGCGCACACAATAAATTTTTTTT    638

Query      61       ttttttttCTGGTTYCGGTTGGTTTGGGGCMCwaaaaaaTTTGRAWRGAAAATTTWCMAT    120
                    ||||||||    |||  |||  ||||  |  |  |  |||||||||    |  ||||| |  ||
Sbjct      639      TTTTTTTTCTTGTTTCTGTTTGTTTTGCGCACTAACAAATTTGTATAGTAAATTTACTAT    698

Query      121      MAAATTTTCGGTTGGGGCccccaaatttccccccawrgttagaaggaccccccccaatt    180
                    |||||||| |||  |  |  |  |  ||||||  ||  ||||||  |||| |  |||||||
Sbjct      699      CAAATTTTCTGTTTGTGTACACACACTTTCCCTCACATAGTTAGACGGACACTCCCAATT    758

Query      181      cccacccmaccaaaaaTTACTCTCTCTCCCCAMTTTTYWWMCCARG-GGaaaaaaaa    239
                    |  ||| |  ||||||  ||||||||||||||| |  |||    |||  ||||  ||||
Sbjct      759      CACACACTACCAACAATTACTCTCTCTCTCACAACTTTCATACCAAGAGGAAGAAAAG    818

Query      240      aaaaaaaaawTTTGGAAATTTTTYCARGTTTCCCCGMCYTTAAATTTTTGTTAAACCCAM    299
                    ||||||  ||  |||  |||||||||| ||  |||  |  |||  |||||||||| ||||||
Sbjct      819      AAAAAAGAATTTT-GAAATTTTTTCAAGTTTTCACGTACTTAGATTTTTGTTTAACCCAA    877

Query      300      TTTCGCCSMGCATATAAAAAAGAA    323
                    | ||  |  ||||||||| ||||
Sbjct      878      TATCAACA-GCATATAATAGAGAA    900
```

FIG. 5

SEQUENCE LISTING

```
<160> NUMBER OF SEQ ID NOS: 16

<210> SEQ ID NO 1
<211> LENGTH: 22
<212> TYPE: DNA
<213> ORGANISM: Artificial Sequence
<220> FEATURE:
<223> OTHER INFORMATION: Synthetic primer

<400> SEQUENCE: 1
actttcgatg gtaggatagt gg                                                22

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2
tgatcgtctt cgatcccta a                                                  21

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
cgtcggtttg gcaaaaagtg                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
tggtaatcta gatgcgccga                                                   20

<210> SEQ ID NO 5
<211> LENGTH: 25
<212> TYPE: DNA
<213> ORGANISM: Artificial Sequence
<220> FEATURE:
<223> OTHER INFORMATION: Synthetic primer

<400> SEQUENCE: 5
acgtgcaaag atttatccat taggg                                             25

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
acccaaatgg acgttggcag                                                   20

<210> SEQ ID NO 7
<211> LENGTH: 20
<212> TYPE: DNA
<213> ORGANISM: Artificial Sequence
```

```
<220> FEATURE:
<223> OTHER INFORMATION: Synthetic primer

<400> SEQUENCE: 7
gcgcgatggc taaccatttt                                                 20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
gacagcatca ccaccgagaa                                                 20

<210> SEQ ID NO 9
<211> LENGTH: 540
<212> TYPE: DNA
<213> ORGANISM: Artificial Sequence
<220> FEATURE:
<223> OTHER INFORMATION: Multiplex PCR amplicon of universal fungal 18s
      rRNA gene

<400> SEQUENCE: 9
cggctaccac atccaaggaa ggcagcaggc gcgcaaatta cccaatcccg acacggggag     60
gtagtgacaa taaataacga tacagggccc ttttgggtct tgtaattgga atgagtacaa    120
tgtaaatacc ttaacgagga acaattggag ggcaagtctg gtgccagcag ccgcggtaat    180
tccagctcca aaagcgtata ttaaagttgt tgcagttaaa aagctcgtag ttgaaccttg    240
ggcttggctg gccggtccat cttttttgatg cgtactggac ccagccgagc ctttccttct    300
gggtagccat ttatggcgaa ccaggacttt tactttgaaa aaattagagt gttcaaagca    360
ggcctttgct cgaatatatt agcatggaat aatagaatag gacgttatgg ttctatttg     420 ttggtttcta ggaccatcgt aatgattaat agggacggtc ggggggtatca gtattcagtt    480 gtcagaggtg aaattcttgg atttactgaa gactaactac tgcgaaagca tttaccaagg    540

<210> SEQ ID NO 10
<211> LENGTH: 540
<212> TYPE: DNA
<213> ORGANISM: Candida albicans

<400> SEQUENCE: 10
cggctaccac atccaaggaa ggcagcaggc gcgcaaatta cccaatcccg acacggggag     60
gtagtgacaa taaataacga tacagggccc ttttgggtct tgtaattgga atgagtacaa    120
tgtaaatacc ttaacgagga acaattggag ggcaagtctg gtgccagcag ccgcggtaat    180
tccagctcca aaagcgtata ttaaagttgt tgcagttaaa aagctcgtag ttgaaccttg    240
ggcttggctg gccggtccat cttttttgatg cgtactggac ccagccgagc ctttccttct    300
gggtagccat ttatggcgaa ccaggacttt tactttgaaa aaattagagt gttcaaagca    360
ggcctttgct cgaatatatt agcatggaat aatagaatag gacgttatgg ttctatttg     420 ttggtttcta ggaccatcgt aatgattaat agggacggtc ggggggtatca gtattcagtt    480 gtcagaggtg aaattcttgg atttactgaa gactaactac tgcgaaagca tttaccaagg    540

<210> SEQ ID NO 11
<211> LENGTH: 244
<212> TYPE: DNA
<213> ORGANISM: Artificial Sequence
```

```
<220> FEATURE:
<223> OTHER INFORMATION: Multiplex PCR amplicon of Klebsiella pneumonia

<400> SEQUENCE: 11
caataagata aggcttatgg agccagtcat ctgcagtcag cggctcggtc ggcgggctgt      60
tccacgcatg cagatgcatg ccgacttccg cggtgccgcg ggcaatcacg tctctggcga     120
attcgatata aagggatcg atggccattt catagttggt caaatagacc ggtttaaagc     180 catactttc gcaaagctgc tgaaaacgcg aagataacg cgcattctcg gtggtgatgc     240
tgtc                                                                  244

<210> SEQ ID NO 12
<211> LENGTH: 244
<212> TYPE: DNA
<213> ORGANISM: Klebsiella pneumoniae

<400> SEQUENCE: 12
caataagata aggcttatgg cgccagtcat ctgcagtcag cggctcggtc ggcgggctgt      60
tccacgcatg cagatgcatg ccgacttccg cggtgccgcg ggcaatcacg tctctggcga     120
attcgatata aaggggtcg atggccattt catagttggt caaatagacc ggtttaaagc     180 catactttc gcaaagctgc tgaaaacgcg gaagataacg cgcattctcg gtggtgatgc     240
tgtc                                                                  244

<210> SEQ ID NO 13
<211> LENGTH: 414
<212> TYPE: DNA
<213> ORGANISM: Artificial Sequence
<220> FEATURE:
<223> OTHER INFORMATION: Multiplex PCR amplicon of Staphylococcus aureus

<400> SEQUENCE: 13
ctactttaga tgcaacataa ccaatattgc cggataatct tccagttaag cgacttttt       60 taaacatatc tccaattaga gaagtaactg tcgttttacc atttgtaccc gttacagcta     120
tgattggkgc ttcararatw arataactta actcaacttc tgttaaaatt ttcaaacctc     180
gtttcmctgc ttcatcaata atagatactg tataaggtat tccaggattt ttaacaatta     240
ttggattatt atcaagcaac gttaatggat gacttccact tacaacaraa atgcccatar     300
attctaaatc ttttgcatga gcatcttgkg ataagtctttt tccatcattg acagttacat     360
tcgcacctaa tttacttaat aatttagctg cttcataacc actttttgcc aaac           414

<210> SEQ ID NO 14
<211> LENGTH: 414
<212> TYPE: DNA
<213> ORGANISM: Staphylococcus aureus

<400> SEQUENCE: 14
ctactttaga tgcaacataa ccaatattgc cggataatct tccagttaag cgacttttt       60 taaacatatc tccaattaga gaagtaactg tcgttttacc atttgtaccc gttacagcta     120
tgattggtgc ttcagagatt agataactta actcaacttc tgttaaaatt ttcaaacctc     180
gtttcactgc ttcatcaata atagatactg tataaggtat tccaggattt ttaacaatta     240
ttggattatt atcaagcaac gttaatggat gacttccact tacaacagaa atgcccatag     300
attctaaatc ttttgcatga gcatcttgtg ataagtctttt tccatcattg acagttacat     360
tcgcacctaa tttacttaat aatttagctg cttcataacc actttttgcc aaac           414
```

```
<210> SEQ ID NO 15
<211> LENGTH: 323
<212> TYPE: DNA
<213> ORGANISM: Artificial Sequence
<220> FEATURE:
<223> OTHER INFORMATION: Multiplex PCR amplicon for Candida albicans

<400> SEQUENCE: 15
tttgtattga tgttgagatc ttactatctt taactatgcg cacacaataa atttttttt      60 tttttttct ggttycggtt ggtttggggc mcwaaaaaat ttgrawrgaa aatttwcmat     120
maaattttcg gttgggggcc cccaaatttc cccccawrg ttagaaggac cccccaatt     180 cccacccmac caaaaattac tctctctctc ccccamtttt ywwmccargg gaaaaaaaaa    240
aaaaaaaawt ttggaaattt ttycargttt ccccgmcytt aaatttttgt taaacccamt    300
ttcgccsmgc atataaaaaa gaa                                            323

<210> SEQ ID NO 16
<211> LENGTH: 322
<212> TYPE: DNA
<213> ORGANISM: Candida albicans

<400> SEQUENCE: 16
tttgtattga tgttgagatc ttactatctt taactatgcg cacacaataa atttttttt      60 tttttttct tgtttctgtt tgttttgcgc actaacaaat ttgtatagta aatttactat    120
caaattttct gtttgtgtac acacactttc cctcacatag ttagacggac actcccaatt    180
cacacactac caacaattac tctctctctc tcacaacttt cataccaaga ggaagaaaag    240
aaaaaagaat tttgaaattt tttcaagttt tcacgtactt agattttgt ttaacccaat    300 atcaacagca tataatagag aa                                             322
```

SEQUENCE SPECIFIC PRIMER POOL FOR MULTIPLEX PCR AND METHOD OF DETECTING MICROBIAL INFECTIONS IN THALASSEMIA PATIENTS

CROSS REFERENCE TO RELATED APPLICATIONS

This application claims the benefit of U.S. Provisional Application No. 62/053,014 filed Sep. 19, 2014.

BACKGROUND OF THE INVENTION

Technical Field

The present invention relates to reagents and methods for the detection of microbial infections in thalassemia patients. More particularly, the present invention relates to unique, sequence specific primer pools for PCR-based methods of detecting microbial infections in thalassemia patients.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Thalassemia is a hereditary blood disorder wherein the body does not produce sufficient hemoglobin, causing a lack of healthy of red blood cells and delivery of oxygen to all cells of the body. People with thalassemia may have mild or severe anemia, and often feel tired, weak and short of breath. Severe anemia can damage organs and lead to death.

The protein hemoglobin is made of two alpha and two beta subunits. When thalassemia is categorized into "alpha" or "beta", this refers to the part of the hemoglobin that is not being produced. When either the alpha or the beta subunits are not being made, there are not enough building blocks to produce normal amounts of hemoglobin.

When the words "trait", "minor", "intermedia" or "major" are used, these words describe the severity of thalassemia. The type of thalassemia that a person has depends on how many and what type of traits for thalassemia a person has inherited, or received from their parents. For instance, a person with beta thalassemia major receives a beta thalassemia trait from both parents. If a person receives an alpha thalassemia trait from a parent and the normal alpha parts from the other parent, he or she would have alpha thalassemia trait (also called alpha thalassemia minor). Having a thalassemia trait means that a person may not have any symptoms, but he or she might pass that trait on to their children and increase their risk for having thalassemia.

Both alpha- and beta-forms of thalassemia major can cause significant complications. For example, people with thalassemia can get too much iron in their bodies, either from the disease itself or from frequent blood transfusions. The iron overload can result in damage to the heart, liver and endocrine system which includes glands that produce hormones that regulate processes throughout the body. Bone deformities are also common since thalassemia can make the bone expand, causing bone to widen. Thalassemia is also often accompanied by the destruction of a large number of red blood cells, making the spleen to work harder than normal and enlarge (splenomegaly). Splenomegaly can make anemia worse and reduce the life of transfused red blood cells. If the spleen grows too big, it will have to be surgically removed.

People with thalassemia major have an increased risk of infection. This is especially true when the spleen has been removed from the patient's body due to the aforementioned severe splenomegaly. Infections are major complications for thalassemia patients and constitute the second most common cause of mortality and morbidity for these patients. Major causative organisms of bacterial infections in thalassemic patients include *Klebsiella* sp., *Candida albicans, Staphylococcus aureus, Yersinia enterocolitica, Pseudomonas* sp. and *Streptococcus pneumoniae*. For most of these bacteria, vaccines are not available. Where infection is suspected, the main causes to be considered include splenectomy, transmission of pathogens by blood transfusions, iron overload and iron chelation. As the body's immune system of a thalassemic patient is already sharply suppressed due to a reduction in neutrophil numbers, it is crucial to reduce mortality by recognizing and presumptively treating infections in a patient as quickly as possible. PCR-based methods are known to facilitate the detection of pathogenic DNA components in biological samples (Vosberg, Human Genetics 83(1):1-15, 1989—incorporated herein by reference in its entirety).

Accordingly, a need exists for methods and reagents for the early detection of bacterial infections in patients of thalassemia major.

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

In a first aspect, the present invention relates to a primer pool, comprising a single-stranded oligonucleotide primer pair for the recognition and amplification of a DNA sequence of at least one Fungi species, a single-stranded oligonucleotide primer pair for the recognition and amplification of a DNA sequence of *Klebsiella pneumoniae*, a single-stranded oligonucleotide primer pair for the recognition and amplification of a DNA sequence of *Candida albicans* and a single-stranded oligonucleotide primer pair for the recognition and amplification of a DNA sequence of *Staphylococcus aureus*. In one embodiment, the primer pairs in the primer pool recognize and simultaneously amplify the 18s rRNA gene from at least one Fungi species, walW gene from *Klebsiella pneumoniae*, the ystI gene from *Candida albicans* and the murD gene from *Staphylococcus aureus*. These primer pairs contain nucleotide sequences as outlined in SEQ ID NOS: 1-8. In some embodiments, the primer pool is included in a kit for the detecting infections by multiple pathogens in a subject human diagnosed with or is suspected of having thalassemia major. The kit comprises a primer pool, reagents and tools for collecting a biological sample from the subject human, reagents for a PCR reaction other than the primer pool, reagents for a cycle sequencing PCR reaction and at least one buffer for DNA resuspension and storage. In one embodiment, the primer pool may contain primer pairs as previously described. Examples of biological samples include skin, plasma, serum, spinal fluid, synovial fluid, lymph fluid, urine, blood cells, sputum, organs and samples of in vitro cell culture constituents.

In a second aspect, the present invention relates to a PCR-based method of detecting infections by multiple pathogens in a subject human diagnosed with or is suspected of having thalassemia major. The method comprises steps of isolating total DNA from the subject human, performing a PCR reaction on the isolated total DNA wherein the PCR reaction comprises a primer pool comprising single-stranded oligonucleotide primer pairs for the simultaneous recognition and amplification of DNA sequences of at least one Fungi species, *Klebsiella pneumoniae, Candida albicans* and *Staphylococcus aureus* and determining the nucleotide sequences of the PCR amplification products wherein the sequences are indicative of the infections. In one embodiment, the primer pool may contain primer pairs as previously described.

In a third aspect, the present invention refers to a primer pool, comprising a single-stranded oligonucleotide primer pair having the nucleotide sequences of SEQ ID NOS: 1 and 2, a single-stranded oligonucleotide primer pair having the nucleotide sequences of SEQ ID NOS: 3 and 4, a single-stranded oligonucleotide primer pair having the nucleotide sequences of SEQ ID NOS: 5 and 6 and a single-stranded oligonucleotide primer pair having the nucleotide sequences of SEQ ID NOS: 7 and 8.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 2 illustrates an excerpt of the alignment of a nucleotide sequence of a multiplex PCR amplicon of universal fungal 18s rRNA gene (SEQ ID NO: 9) with a known sequence of a corresponding region (SEQ ID NO: 10).

FIG. 3 illustrates an excerpt of the alignment of a nucleotide sequence of a multiplex PCR amplicon of *Klebsiella pneumoniae* (SEQ ID NO: 11) with a known sequence of a corresponding region (SEQ ID NO: 12).

FIG. 4 illustrates an excerpt of the alignment of a nucleotide sequence of a multiplex PCR amplicon of *Staphylococcus aureus* (SEQ ID NO: 13) with a known sequence of a corresponding region (SEQ ID NO: 14).

FIG. 5 illustrates an excerpt of the alignment of a nucleotide sequence of a multiplex PCR amplicon of *Candida albicans* (SEQ ID NO: 15) with a known sequence of a corresponding region (SEQ ID NO: 16).

DETAILED DESCRIPTION OF THE EMBODIMENTS

Figure 1:
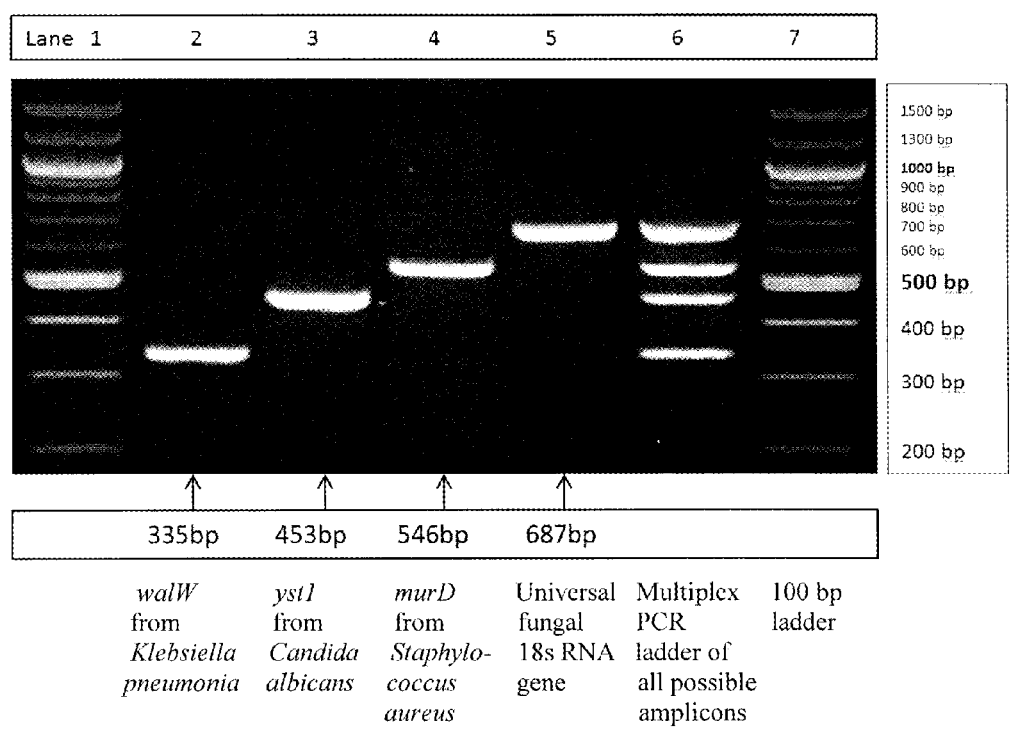
FIG. 1 is an image of an agarose gel illustrating amplicons of single PCR reactions and a multiplex PCR reaction.

Referring now to the drawings, wherein like reference numerals designate identical or corresponding parts throughout the several views. All patents, patent applications, and publications mentioned herein, both supra and infra, are hereby incorporated by reference in their entirety.

The present invention pertains to methods and reagents for the simultaneous accurate and fast early detection of infections and sepsis by multiple pathogens in patients diagnosed with or is suspected of having thalassemia major. These methods and reagents may also be used to determine the prevalence of microbial infections in thalassemia major patients in a regional population. Such infections may occur as a result of complications of anemia, splenectomy, iron overload, iron chelation and blood transfusions. In one embodiment, the pathogens may be bacteria, virus, fungus (*Mucor* sp), protozoa (*Plasmodium* sp) or combinations thereof. Examples of the infectious bacteria include but are not limited to *Klebsiella pneumoniae, Candida albicans, Staphylococcus aureus, Yersinia enterocolitica, Pseudomonas* sp. *Escherichia coli, Vibrio vulnificus, Salmonella* sp, *Neisseria meningtidis* and *Streptococcus pneumoniae.* Examples of viruses commonly associated with chronic infections in thalassemic patients include the human parvovirus B-19, human cytomegalovirus, hepatitis A virus, hepatitis B virus, hepatitis C virus, human immunodeficiency virus, human herpes virus, Epstein-Barr virus, transfusion-transmitted virus.

In one embodiment, methods described herein detect fungal infections and infections by bacteria *Klebsiella pneumoniae, Candida albicans* and *Staphylococcus aureus.*

Methods disclosed herein are effective in detecting the presence of at least one of these pathogens or combinations thereof. Detection of the presence of pathogens and identification of the species are based upon the detection of a gene with a nucleotide sequence specific to the bacterial species. Methods include an initial step of collecting a biological sample from a thalassemic patient. For purposes of the invention, a "biological sample" refers to a sample of tissue or fluid isolated from an individual diagnosed with or is suspected of having thalassemia major, including but not limited to, for example, skin, plasma, serum, spinal fluid, synovial fluid, lymph fluid, urine, blood cells, sputum, organs, and also samples of in vitro cell culture constituents. These biological samples may also concurrently be tested for microbial infections using conventional plating methods.

Total DNA may be isolated and purified from the collected biological sample. Total DNA includes a mixture of genomic DNA of a thalassemic patient as well as genomic DNA of all pathogens infecting the patient suspended in a standard buffer for DNA storage such as Tris-EDTA at concentrations anywhere between 10 μM and 500 μM. In one embodiment, total DNA may include the a mixture of genomic DNA from a thalassemic patient and at least one of the following pathogens: *Klebsiella pneumoniae, Candida albicans, Staphylococcus aureus* and any species from all four major phyla of Fungi: Ascomycota, Basidiomycota, Chytridomycota and Zygomycota.

Methods also entail a multiplex PCR reaction wherein target genes belonging to different bacterial species may be amplified simultaneously in a single tube of PCR reaction.

As used herein, the terms "polynucleotide" and "oligonucleotide" refer to primers, probes, oligomer fragments to be detected, oligomer controls and unlabeled blocking oligomers and shall be generic to polydeoxy-ribonucleotides (containing 2-deoxy-D-ribose), to polyribonucleotides (containing D-ribose), and to any other type of polynucleotide which is an N-glycoside of a purine or pyrimidine base, or modified purine or pyrimidine bases. There is no intended distinction in length between the term "polynucleotide" and "oligonucleotide", and these terms will be used interchangeably. These terms refer only to the primary structure of the molecule. Thus, these terms include double- and single-stranded DNA, as well as double- and single-stranded RNA.

The term "primer" may refer to more than one primer and refers to a single-stranded oligonucleotide, whether occurring naturally, as in a purified restriction digest, or produced synthetically, which is capable of acting as a point of initiation of synthesis along a complementary strand when placed under conditions in which synthesis of a primer extension product or amplicon, as used herein, which is complementary to a nucleic acid strand is catalyzed.

Such conditions include the presence of four different deoxyribonucleoside triphosphates and a polymerization-inducing agent such as a thermostable nucleotide polymerase, DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification.

As used herein, the term "target sequence" refers to a region of the polynucleotide which is to be amplified and/or detected. "Target gene" refers to a target sequence wherein the region of the polynucleotide is a full functional gene of an organism that codes for a polypeptide or for an RNA chain that has a function in the organism.

As used herein, the term "thermostable nucleotide polymerase" refers to an enzyme which is relatively stable to heat when compared to nucleotide polymerases from *E. coli* and which catalyzes the polymerization of nucleosides. Generally, the enzyme will initiate synthesis at the 3'-end of the target sequence utilizing the primer, and will proceed in the 3'-direction along the template until synthesis terminates. A representative thermostable enzyme isolated from *Theymus aquaticus* (Taq) is described in U.S. Pat. No. 4,889,818 and a method for using it is described in Saiki et al., (1988), Science 239:487 (both incorporated herein by reference in their entirety).

The practice of the present invention will employ, unless otherwise indicated, conventional techniques of molecular biology, microbiology and recombinant DNA techniques, which are within the skill of the art. Such techniques are explained fully in the literature and specific recipes and conditions for PCR reactions are provided in the examples below. (See, e.g., Sambrook, Fritsch & Maniatis, Molecular Cloning; A Laboratory Manual, Second Edition, (1989) (hereinafter "Maniatis"); Oligonucleotide Synthesis (M. J. Gait, ed., 1984); Nucleic Acid Hybridization (B. D. Hames & S. J. Higgins, eds., 1984); A Practical Guide to Molecular Cloning (B. Perbal, 1984); and a series, Methods in Enzymology (Academic Press, Inc.)—each incorporated herein by reference in its entirety).

Additionally, the present invention relates to a primer pool comprising multiple primer pairs that recognize, anneal to and simultaneously amplify targeted genes of multiple bacterial species. Typically, the length of a bacterial gene is no greater than 3000 bp, preferably 300 bp to 2500 bp or 300 bp to 1000 bp. Therefore, the corresponding amplification products or amplicons from the multiplex PCR reaction will also have the same size. In one embodiment, the targeted bacterial genes are walW from *Klebsiella pneumoniae* (335 bp), ystI from *Candida albicans* (453 bp) and murD from *Staphylococcus aureus* (546 bp) (see FIG. 1).

For the detection of fungal infections, the primer pool may further comprise a primer pair for the universal recognition of the fungal 18s rRNA gene that is capable of recognizing the 18s rRNA gene of all known strains from all four major phyla of Fungi: Ascomycota, Basidiomycota, Chytridiomycota and Zygomycota. As can be seen from the agarose gel image of stained DNA amplicons viewed under the UV-light, the fungal 18s rRNA gene or its amplicon has a size of 687 bp. Table 1 summarizes the primers included in the primer pool according to one embodiment of the present invention, the organisms of origin, sequence ID numbers, length of primers, melting temperatures of the primers and size of products. The specific nucleotide sequences of the primers are submitted separately from this specification in compliance with 37 CFR Sections 1.821-1.825.

TABLE 1

Primer sequences in an exemplary primer pool for the simultaneous recognition and amplification of target genes fungal 18s RNA gene, walW from *Klebsiella pneumoniae*, yst1 from *Candida albicans* and murD from *Staphylococcus aureus* in a multiplex PCR reaction.

| Organism | Gene | SEQ ID NO | Length (bp) | $T_m$ (° C.) | Amplicon size (bp) |
|---|---|---|---|---|---|
| Fungi | Universal 18s RNA gene | 1 (forward) | 22 | 57.06 | 687 |
|  |  | 2 (reverse) | 21 | 58.06 |  |
| *Staphylococcus aureus* | murD | 3 (forward) | 20 | 58.8 | 546 |
|  |  | 4 (reverse) | 20 | 58.6 |  |
| *Candida albicans* | yst1 | 5 (forward) | 25 | 59.7 | 453 |
|  |  | 6 (reverse) | 20 | 61.18 |  |
| *Klebsiella pneumoniae* | walW | 7 (forward) | 20 | 59.90 | 335 |
|  |  | 8 (reverse) | 20 | 60.04 |  |

In designing a target specific primer pool for amplifying genes specific to pathogenic DNA component by a simple multiplex PCR, the following parameters are taken into consideration. An oligonucleotide primer of a target specific primer pool binds to a target sequence of a particular gene of interest in pathogenic DNA component and should not interfere with each other. Therefore, the length of the PCR amplicons should differ by at least 90 bp to 140 bp or about 100 bp so that the difference can be visually observed on a DNA agarose gel after electrophoretic separation. Any primer pair should be able to efficiently amplify a target specific pathogenic DNA sequence in a sufficient amount, and does not interfere with the remaining primers from the primer pool. Each oligonucleotide primer of a target specific primer pool has a similar or nearby annealing temperature. Any two individual primers of the primer pool should not form primer self-dimers or hairpin loops.

Target specific primers according to the present invention may be chosen manually using sequences available in the NCBI (National Center for Biotechnology Information) and validated using the Basic Local Alignment Search Tool (BLAST) and web based PRIMER3 (Untergrasser et al., Nucleic Acids Research 40(15):e115, 2012; Koressaar and Remm, Bioinformatics 23(10):1289-1291, 2007—each incorporated herein by reference in its entirety). Computational primer design programs like PRIMER3 are equipped with algorithms to enhance primer annealing to the templates as well as to circumvent designs that encourage the formation of primer dimers and hairpin loops.

The multiplex PCR reaction according to one embodiment of the present invention may be carried out as follows:

A total DNA sample prepared as described previously is provided which is suspected of containing a particular nucleic acid sequence of interest, the "target sequence" or a "target gene" if the sequence of interest covers an entire gene. The nucleic acid contained in the sample may be first reverse transcribed into cDNA, if necessary, and then denatured, using any suitable denaturing method, including physical; chemical, or enzymatic means, which are known to those of skill in the art. A preferred physical means for strand separation involves heating the nucleic acid until it is completely (>99%) denatured. Typical heat denaturation involves temperatures ranging from about 80° C. to about 105° C., for times ranging from about 1 to 10 min.

The denatured DNA strands are then incubated with the selected oligonucleotide primers under hybridization conditions, conditions which enable the binding of the primers to the single oligonucleotide strands. As known in the art, the primers are selected so that their relative positions along a duplex sequence are such that an extension product synthesized from one primer, when it is separated from its complement, serves as a template for the extension of the other primer to yield a replicate chain of defined length. The primer must be sufficiently long to prime the synthesis of extension products in the presence of the agent for polymerization. The exact length of the primers will depend on many factors, including temperature, source of the primer and use of the method. For example, depending on the complexity of the target sequence, the oligonucleotide primer typically contains about 15-35 nucleotides or 15-35 bp, although it may contain more or fewer nucleotides. Short primer molecules generally require cooler temperatures to form sufficiently stable hybrid complexes with the template. The primers must be sufficiently complementary to selectively hybridize with their respective strands.

The primers used herein are selected to be "substantially" complementary to the different strands of each specific sequence to be amplified. The primers need not reflect the exact sequence of the template, but must be sufficiently complementary to selectively hybridize with their respective strands. This is especially true for the case of the fungal 18s RNA gene wherein slight variations in nucleotide sequence occur between fungal species. Non-complementary bases or longer sequences can be interspersed into the primer, provided that the primer retains sufficient complementarity with the sequence of one of the strands to be amplified to hybridize therewith, and to thereby form a duplex structure which can be extended by the polymerizing means. The non-complementary nucleotide sequences of the primers may include restriction enzyme sites. Appending a restriction enzyme site to the end(s) of the target sequence is particularly helpful for subsequent cloning of the target sequence.

Exemplary cycling conditions for a multiplex PCR reaction of the present invention may read as follows: 95° C. for 4 min; 18-35 cycles of 95° C. for 30 s, 58° C. for 1 min, 72° C. for 1 min; 72° C. for 5 min; then incubate at 4° C. until the next step in the protocol.

An exemplary multiplex PCR reaction may comprise the following components: 10 µl of $MgCl_2$ (1.5 mM); 1 µl of dNTP mix (10 mM); 5 µl of 10×Taq DNA polymerase buffer; 2-8 µl of primer pool mixture (at least one forward and reverse primer pairs in Table 1 or combinations thereof mixed to a final concentration of 15 pM); 1 µl of total DNA as template DNA (100 ng) and 0.25 µl of Taq polymerase (5 U/µl). Sterilized, nuclease-free water is added to the reaction mixture to a final volume of 50 µl.

Any commercially available thermal cycler, such as T professional basic thermal cycler gradient, Biometra; Mastercycler, Eppendorf, MyCycler, or BioRad, may be used to perform the temperature profile. The PCR amplicons may be electrophoresed with 0.8-1.5% agarose gel, as shown in FIG. 1.

Methods disclosed herein further include methods of identifying all amplicons generated from the aforementioned multiplex PCR reaction through DNA sequencing analysis. In general, separate cycle sequencing PCR reactions are performed by using the four multiplex PCR amplicons as template DNA and respective forward (SEQ ID NOS: 1, 3, 5 or 7) or reverse (SEQ ID NOS: 2, 4, 6 or 8) primers for each amplicon as the sequencing primer. Dideoxynucleotides (ddNTP) such as ddATP, ddTTP, ddCTP and ddGTP are used instead of deoxynucleotides for standard PCR reactions so that the extension of the DNA may be interrupted, according to the concept of Sanger sequencing (Sanger F and Coulson A R, A rapid method for determining sequences in DNA by primer synthesis with DNA polymerase, J Mol Biol 94(3):441-448, 1975—incorporated herein by reference in its entirety). Also according to the Sanger sequencing method, the ddNTP may include tagging with radiolabeling or a fluorescent dye.

After the cycle sequencing PCR reactions, capillary electrophoresis is performed for individual cycle sequence products. The capillary electrophoresis may be conducted using Genetic Analyzer 3500 (Applied Biosystems). Nucleotide sequences of all amplicons are aligned with a corresponding known sequences of respective genes as shown in FIGS. 2-5. Bioinformatics tools such as ClustalW2 may be used to perform the sequence alignment to identify regions of sequence similarity and homology between a cycle sequencing PCR product according to various embodiments the present invention and its respective reference sequence. Examples of these sequence alignment results are shown in FIGS. 2-5.

As shown in an example in FIG. 2, an excerpt of the sequence of the fungal 18s rRNA gene (SSU) for universal fungal sequence amplified by a multiplex PCR using the primer pair according to SEQ ID NOS: 1 and 2 (Query; SEQ ID NO: 9) exhibits a homology of 99% with a corresponding reference sequence (Subject; SEQ ID NO: 10).

An excerpt of the sequence of walW gene from *Klebsiella pneumoniae* amplified by a multiplex PCR using the primer pair according to SEQ ID NOS: 7 and 8 (Query; SEQ ID NO: 11) shows a homology of 98% (see FIG. 3) with another corresponding reference sequence (Subject; SEQ ID NO: 12).

An excerpt of the sequence of murD gene from *Staphylococcus aureus* amplified by a multiplex PCR using the primer pair according to SEQ ID NOS: 3 and 4 (Query, SEQ ID NO: 13) shows a homology of 95% (see FIG. 4) with another corresponding reference sequence (Subject; SEQ ID NO: 14).

Similarly, an excerpt of the sequence of ystI gene from *Candida albicans* amplified by a multiplex PCR using the primer pair having SEQ ID NOS: 5 and 6 (Query; SEQ ID NO: 15) possesses a homology of 79% (see FIG. 5) with yet another corresponding sequence (Subject; SEQ ID NO: 16).

A low nucleotide sequence alignment homology may sometimes happen as a result of poor yield from cycle sequencing PCR reactions. Adjustments to the concentrations of the ddNTP, template DNA and primers may enhance the yield of the cycle sequencing PCR products.

Finally, the present invention also relates to a kit for the detection of infections in thalassemia major patients. The kit may include the primer pool including all embodiments described herein, as well as tools for collection of biological samples, reagents for multiplex and cycle sequencing PCR reactions and buffer for DNA resuspension storage. The primer pool may be supplied in a lyophilized state so that it is temperature sensitive and may be stored at room temperature. The DNA polymerases, dNTPs and ddNTPs may be stored at 4° C. during transportation or −20° C. for long term storage.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method of detecting infections by multiple pathogens in a human subject diagnosed with or suspected of having thalassemia major, comprising:
   (a) isolating total DNA from a biological sample obtained from the human subject;
   (b) performing a PCR reaction on the isolated total DNA wherein the PCR reaction comprises a primer pool comprising single-stranded oligonucleotide primer pairs for simultaneous recognition and amplification of DNA sequences of *Klebsiella pneumoniae, Candida albicans, Staphylococcus aureus* and at least one fungi species; and
   (c) determining the nucleotide sequences of PCR amplification products from (b) wherein presence of PCR amplification products from two or more of *Klebsiella pneumoniae, Candida albicans, Staphylococcus aureus* and/or at least one fungi species is indicative of multiple infection; wherein the primer pairs have the nucleotide sequences of SEQ ID NOS. 1-8.

2. The method of claim 1, wherein the biological sample is blood, plasma or serum.

3. The method of claim 1, wherein the biological sample is spinal fluid.

4. The method of claim 1, wherein the biological sample is synovial fluid.

5. The method of claim 1, wherein the biological sample is lymph fluid.

6. The method of claim 1, wherein the biological sample is sputum.

7. The method of claim 1, wherein the biological sample is urine.

8. The method of claim 1, wherein the biological sample comprises cells.

9. The method of claim 1, wherein the biological sample comprises cells from the subject that have been cultured in vitro.

* * * * *